(12) United States Patent
Garcia Jimenez et al.

(10) Patent No.: US 11,517,536 B2
(45) Date of Patent: Dec. 6, 2022

(54) PHARMACEUTICAL COMPOSITION COMPRISING POMALIDOMIDE

(71) Applicant: SYNTHON B.V., Nijmegen (NL)

(72) Inventors: Sonia Garcia Jimenez, Sant Boi de Llobregat (ES); Luis Nogueiras Nieto, Sant Boi de Llobregat (ES); Lisardo Alvarez Fernandez, Sant Boi de Llobregat (ES); Jose Velada Calzada, Nijmegen (NL)

(73) Assignee: Synthon B.V., Nijmegen (NL)

( * ) Notice: Subject to any disclaimer, the term of this patent is extended or adjusted under 35 U.S.C. 154(b) by 197 days.

(21) Appl. No.: 16/322,571

(22) PCT Filed: Jul. 28, 2017

(86) PCT No.: PCT/EP2017/069242
§ 371 (c)(1),
(2) Date: Feb. 1, 2019

(87) PCT Pub. No.: WO2018/024646
PCT Pub. Date: Feb. 8, 2018

(65) Prior Publication Data
US 2019/0183805 A1 Jun. 20, 2019

(30) Foreign Application Priority Data
Aug. 2, 2016 (EP) .................... 16182389

(51) Int. Cl.
*A61K 31/454* (2006.01)
*A61K 9/48* (2006.01)
(52) U.S. Cl.
CPC .......... *A61K 9/4866* (2013.01); *A61K 9/4858* (2013.01); *A61K 31/454* (2013.01)

(58) Field of Classification Search
CPC .. A61K 31/454; A61K 9/4858; A61K 9/4866; A61K 9/48
See application file for complete search history.

(56) References Cited

U.S. PATENT DOCUMENTS

| | | | | |
|---|---|---|---|---|
| 2011/0045064 A1* | 2/2011 | Tutino | .................... | A61K 47/10 424/452 |
| 2016/0039785 A1* | 2/2016 | Stahly | .................... | C07C 305/04 514/323 |

FOREIGN PATENT DOCUMENTS

| | | | | |
|---|---|---|---|---|
| CN | 104042590 | 9/2014 | | |
| CN | 104224723 | 12/2014 | | |
| CN | 104523692 | 4/2015 | | |
| WO | WO 2010/135396 | * 11/2010 | ............... | A61K 9/48 |
| WO | WO 2010/135396 A2 | 11/2010 | | |

OTHER PUBLICATIONS

Guajardo-Flores et al. Molecules 2015, 20, 21626-21635 and Supplemental material.*
Nazzal et al. Pharmaceutical Technology 2001, 86-98.*

* cited by examiner

*Primary Examiner* — Irina Neagu
(74) *Attorney, Agent, or Firm* — Buscher Patent PLLC

(57) ABSTRACT

The present invention relates to a pharmaceutical composition comprising pomalidomide, maltodextrin and a filler, wherein the weight ratio of maltodextrin to filler ranges from 1:1 to 1:2. The invention further relates to the use of said pharmaceutical composition as medicament in the treatment of multiple myeloma.

12 Claims, No Drawings

PHARMACEUTICAL COMPOSITION COMPRISING POMALIDOMIDE

BACKGROUND OF THE PRESENT INVENTION

Pomalidomide, chemically 4-amino-2-(2,6-dioxopiperidin-3-yl)isoindole-1,3-dione of formula (I),

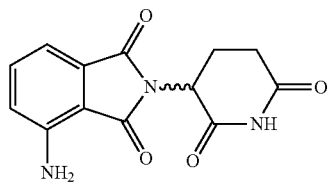

is an anti-angiogenic and also acts as an immunomodulator in the treatment of multiple myeloma. Pomalidomide is marketed by Celgene under the brand names Imnovid® and Pomalyst®. Imnovid® and Pomalyst® are supplied for oral administration, as immediate-release hard gelatin capsules in four different strengths: 1, 2, 3 and 4 mg.

Pomalidomide is a BCS class IV product, having low permeability and low solubility. The drug substance is practically insoluble in water.

WO2010135396 discloses the marketed formulation of Imnovid® and Pomalyst® containing, besides pomalidomide, pregelatinized starch, mannitol and sodium stearyl fumarate. It contains pomalidomide polymorph A. The primary packaging of the capsules is polyvinyl chloride (PVC)/polychlorotrifluoroethylene (PCTFE) blisters with push through aluminium foil. These blisters provide a high moisture barrier, but are expensive.

According to the information published by the EMA in the European Public Assessment Report (EPAR), the capsule strengths use two common blends comprising the same excipients, varying in the proportion of drug substance and the two excipients mannitol and sodium stearyl fumarate. The capsules comprising 1 and 2 mg of pomalidomide are dose proportional and utilize a common blend. The capsules comprising 3 and 4 mg of pomalidomide are dose proportional and use another common blend.

CN104042590 discloses capsule formulations comprising pomalidomide, anhydrous lactose, dextrin, cross-linked sodium carboxymethyl cellulose and polyethylene glycol 4000. It describes the use of two common blends: one blend for the 1 and 2 mg capsules and a second common blend for the 3 and 4 mg capsules. The capsules show good stability at 25° C./60% RH in non-specified packaging material.

CN104224723 discloses pomalidomide nanoparticles comprising 0.5 to 1.5% by weight of pomalidomide. To obtain the nanoparticles, specific equipment is needed which is not present in most pharmaceutical production plants. No stability data of the obtained compositions is presented.

CN104523692 discloses complexes of pomalidomide and cyclodextrins, obtained by freeze-drying. The technique of freeze-drying requires specific equipment and is rather expensive.

In view of the prior art cited above, there is still a need for pharmaceutical compositions comprising pomalidomide, which exhibit excellent long term stability and which are suitable for production on commercial scale by applying techniques and equipment commonly used in industry. It would be advantageous if, in addition, these compositions would require the use of just one common blend for the proposed capsule strengths.

BRIEF DESCRIPTION OF THE PRESENT INVENTION

The present invention provides a pharmaceutical composition comprising pomalidomide, maltodextrin and a filler, wherein the weight ratio of maltodextrin to filler ranges from 1:1 to 1:2.

It also provides a process to prepare said composition in the form of a capsule by blending pomalidomide and excipients followed by encapsulation.

Said pharmaceutical composition may be used as medicament in the treatment of multiple myeloma.

DETAILED DESCRIPTION OF THE PRESENT INVENTION

The marketed formulation of Imnovid® and Pomalyst® contains, besides pomalidomide, pregelatinized starch, mannitol and sodium stearyl fumarate. According to the information published by the EMA in the European Public Assessment Report (EPAR), several formulations were evaluated during development. The first formulation developed contained anhydrous lactose, microcrystalline cellulose, croscarmellose sodium and magnesium stearate. In an effort to improve processing, anhydrous lactose was replaced with anhydrous dibasic calcium phosphate and other excipients were changed accordingly. The revised formulation contained pomalidomide, anhydrous dibasic calcium phosphate, pregelatinized starch, croscarmellose sodium and sodium stearyl fumarate. However, this formulation gave rise to instability at accelerated and room temperature conditions. To overcome the instability of the formulation, additional formulations were studied, resulting in the selection of the currently marketed formulation. The problems ran into during the development of Imnovid® and Pomalyst® show that selection of excipients for this product is a difficult task. Pomalidomide exhibits potential reactivity towards fillers like maltose, lactose, trehalose or glucose, e.g. mono- or disaccharides, via a Maillard reaction. In addition, it seems that pomalidomide is prone to reaction with nucleophiles like calcium phosphate and sodium bicarbonate by a type of Gabriel reaction.

The primary packaging of the marketed capsules is polyvinyl chloride (PVC)/polychlorotrifluoroethylene (PCTFE) blisters with push through aluminium foil. These blisters provide a high moisture barrier, but are expensive. It would be advantageous to have a pharmaceutical composition that does not require such expensive high moisture barrier blister pack material, but that does show sufficient long term stability in less protective packaging material.

The marketed formulation is available as immediate-release hard gelatin capsules in four different strengths: 1, 2, 3 and 4 mg. The capsule strengths are manufactured using two common blends comprising the same excipients, varying in the proportion of drug substance and the two excipients mannitol and sodium stearyl fumarate. The capsules comprising 1 and 2 mg of pomalidomide are dose proportional and utilize one single common blend. The capsules comprising 3 and 4 mg of pomalidomide are dose proportional and use another common blend. It would be advantageous to have a pharmaceutical composition comprising pomalidomide enabling the use of just one blend for all capsule strengths.

It was surprisingly found that a pharmaceutical composition comprising pomalidomide, maltodextrin and a filler, wherein the weight ratio of maltodextrin to filler ranges from 1:1 to 1:2 does not require high moisture barrier packaging material. The compositions of the present invention are more stable in less protective packaging material when compared to the marketed pomalidomide capsules.

Maltodextrin is a saccharide mixture of polymers that consist of D-glucose units, with a dextrose equivalent (DE) less than 20. The solubility, hygroscopicity and compressibility of maltodextrin increase as the DE increases. In principle, any maltodextrin can be used in accordance with the present invention. In a preferred embodiment of the present invention, maltodextrin with a DE of 11 to 14 is selected because of its good flow properties and acceptable bulk density. A typical example of such a grade of maltodextrin is Glucidex 12 or Glucidex IT12.

The pharmaceutical composition of the present invention comprises, besides pomalidomide and maltodextrin, a filler. The weight ratio of maltodextrin to the filler ranges from 1:1 to 1:2. More preferably, the weight ratio of maltodextrin to the filler ranges from 1:1.2 to 1:1.5. Preferably, the filler is selected from microcrystalline cellulose and calcium lactate. Calcium lactate can exist in a number of hydration states. In pharmaceutical compositions, calcium lactate is preferably used in its pentahydrated form as filler. More preferably, the filler used in accordance with the present invention is microcrystalline cellulose. Different grades of microcrystalline cellulose can be used. Most preferably, a type of microcrystalline cellulose with increased bulk density is used, allowing a reduction in blend volumes. A typical example of such a grade of microcrystalline cellulose is Vivapur® 301 or Vivapur® 302. By using the specific weight ratios of maltodextrin to the selected fillers, stable formulations are obtained that are able to mimic the dissolution profile of the Imnovid® and Pomalyst® capsules.

Preferably, the amount of pomalidomide in the pharmaceutical composition in accordance with the present invention is more than 2% by weight based on the total weight of the composition. By using this amount of API in combination with the specified excipients, the pharmaceutical composition according to the present invention requires just one single blend for all capsule strengths while the same capsule size as the Imnovid® and Pomalyst® capsules can be employed. The production process is simpler and the costs are reduced in case all capsule strengths are dose proportional.

In order to mimic the dissolution profile of the Imnovid® and Pomalyst® capsules, Pomalidomide in accordance with the present invention has a particle size distribution $D_{90}$ equal to or less than 15 μm. With increasing $D_{90}$ values, the dissolution is slowing down rapidly.

The pharmaceutical composition of the present invention comprising pomalidomide, maltodextrin and a filler, further comprises one or more pharmaceutically acceptable excipients. The excipients to be used in accordance with the present invention are well-known and are those excipients which are conventionally used by the person skilled in the art. Depending on the dosage form chosen for the pharmaceutical composition, the person skilled in the art will be able to select suitable pharmaceutically acceptable excipients. Preferably, the pharmaceutical composition is in the form of a capsule. Most preferably, the capsule is a hard gelatin capsule.

The pharmaceutical composition of the present invention further comprises, besides pomalidomide, maltodextrin and a filler, a lubricant and optionally a disintegrant.

The lubricant to be used in accordance with the present invention may be any lubricant known to a person of ordinary skill in the art. Sodium stearyl fumarate is a particularly preferred lubricant.

Whether the use of disintegrant in the composition is required depends upon the choice of filler. Some fillers, like microcrystalline cellulose, do possess disintegrating properties. In case such a filler is used, there is no need to include a disintegrant in the pharmaceutical composition. On the other hand, in the event that calcium lactate is used as filler, a disintegrant is required. The disintegrant to be used in accordance with the present invention may be any disintegrant known to a person of ordinary skill in the art. Suitable disintegrants to be used in accordance with the present invention are selected from the group consisting of croscarmellose sodium, crospovidone or sodium starch glycolate. Croscarmellose sodium is a particularly preferred disintegrant.

The pharmaceutical composition in accordance with the present invention exhibits a dissolution rate of at least 65% in 15 minutes and at least 90% in 45 minutes when tested in aqueous hydrochloric acid 0.1 N in a USP apparatus II at 50-100 rpm, 37° C.

The pharmaceutical composition of the present invention exhibits excellent long term stability. It is significantly less sensitive to moisture than the commercial products Imnovid® and Pomalyst® and therefore does not require expensive high moisture barrier packaging material like polyvinyl chloride (PVC)/polychlorotrifluoroethylene (PCTFE) blisters. The capsules of the present invention show excellent stability in e.g. the cheaper triplex (polyvinyl chloride (PVC)/polyethylene (PE)/polyvinylidene chloride (PVDC)) blisters. Even after 6 months at 40° C./75% RH in triplex blisters, the dissolution profile of the capsules mimic the profile of the Imnovid® and Pomalyst® capsules. Moreover, the pharmaceutical composition of the present invention is very suitable for production on commercial scale making use of equipment and techniques commonly used in industry.

The pharmaceutical composition of the present invention in the form of a capsule is obtained by a process comprising blending pomalidomide and excipients followed by encapsulation, using equipment and methods well-known in the art.

The pharmaceutical composition in accordance with the present invention may be used as a medicament. The pharmaceutical composition typically may be used in the treatment of multiple myeloma.

The following examples are intended to illustrate the scope of the present invention but not to limit it thereto.

EXAMPLES

Reference Example 1

Pharmaceutical Composition Imnovid®/Pomalyst®

Imnovid®/Pomalyst® capsules have the composition as given in table 1.

TABLE 1

| Component | Quantity (mg/capsule) | Quantity (mg/capsule) | Quantity (mg/capsule) | Quantity (mg/capsule) |
|---|---|---|---|---|
| Pomalidomide | 1.000 | 2.000 | 3.000 | 4.000 |
| Pregelatinized starch | 70.00 | 140.00 | 100.80 | 134.40 |
| Sodium stearyl fumarate | 0.32 | 0.64 | 0.45 | 0.60 |
| Spray dried mannitol | 53.68 | 107.36 | 75.75 | 101.00 |
| Capsule content weight | 125.00 | 250.00 | 180.00 | 240.00 |
| Capsule size | Size 4 | Size 2 | Size 2 | Size 2 |

The pomalidomide and mannitol were sieved through a suitable mesh sieve for deagglomeration and mixed in a suitable tumbling mixer. Pregelatinized starch was sieved through a suitable mesh sieve for deagglomeration, added to the blend and mixed in the tumbling mixer. Sodium stearyl fumarate was sieved through a suitable mesh sieve to deagglomerate, added to the blend and mixed in the tumbling mixer. The homogeneous blend was encapsulated using a dosator capsule filling machine. The hard gelatin capsules were packed and stored at 40° C./75% RH.

Example 1

Pharmaceutical Composition Comprising Pomalidomide, Microcrystalline Cellulose and Maltodextrin The capsules comprising pomalidomide, microcrystalline cellulose and maltodextrin have the composition as given in table 2.

TABLE 2

| Component | Quantity (mg/capsule) | Quantity (mg/capsule) | Quantity (mg/capsule) | Quantity (mg/capsule) |
|---|---|---|---|---|
| Pomalidomide | 1.000 | 2.000 | 3.000 | 4.000 |
| Microcrystalline cellulose | 26.600 | 53.200 | 79.800 | 106.400 |
| Maltodextrin | 19.781 | 39.563 | 59.344 | 79.125 |
| Sodium stearyl fumarate | 0.119 | 0.238 | 0.356 | 0.475 |
| Capsule content weight | 47.500 | 95.000 | 142.500 | 190.000 |
| Capsule size | Size 4 | Size 2 | Size 2 | Size 2 |

The pomalidomide and microcrystalline cellulose were sieved through a suitable mesh sieve for deagglomeration and mixed in a suitable tumbling mixer. Maltodextrin (Glucidex IT12) was sieved through a suitable mesh sieve for deagglomeration, added to the blend and mixed in the tumbling mixer. Sodium stearyl fumarate was sieved through a suitable mesh sieve to deagglomerate, added to the blend and mixed in the tumbling mixer. The homogeneous blend was encapsulated using a dosator capsule filling machine. The hard gelatin capsules were packed and stored at 40° C./75% RH.

The capsules obtained exhibited a dissolution rate of at least 65% in 15 minutes and at least 90% in 45 minutes when tested in aqueous hydrochloric acid 0.1 N in a USP apparatus II at 100 rpm, 37° C. The dissolution profile of the capsules is similar to the profile of Imnovid®/Pomalyst®.

The capsules obtained are bioequivalent to the Imnovid®/Pomalyst® capsules.

Example 2

Pharmaceutical Composition Comprising Pomalidomide, Calcium Lactate and Maltodextrin The capsules comprising of pomalidomide, calcium lactate and maltodextrin have the composition as given in table 3.

TABLE 3

| Component | Quantity (mg/capsule) | Quantity (mg/capsule) | Quantity (mg/capsule) | Quantity (mg/capsule) |
|---|---|---|---|---|
| Pomalidomide | 1.000 | 2.000 | 3.000 | 4.000 |
| Calcium lactate pentahydrate | 25.89 | 51.78 | 77.66 | 103.550 |
| Maltodextrin | 19.07 | 38.14 | 57.21 | 76.275 |
| Croscarmellose sodium | 1.425 | 2.850 | 4.275 | 5.700 |
| Sodium stearyl fumarate | 0.119 | 0.238 | 0.356 | 0.475 |
| Capsule content weight | 47.500 | 95.000 | 142.500 | 190.000 |
| Capsule size | Size 4 | Size 2 | Size 2 | Size 2 |

The pomalidomide, maltodextrin (Glucidex IT12), calcium lactate pentahydrate and croscarmellose sodium were sieved through a suitable mesh sieve for deagglomeration and mixed in a suitable tumbling mixer. Sodium stearyl fumarate was sieved through a suitable mesh sieve to deagglomerate, added to the blend and mixed in the tumbling mixer. The homogeneous blend was encapsulated using a dosator capsule filling machine. The hard gelatin capsules were packed and stored at 40° C./75% RH.

The capsules obtained exhibited a dissolution rate of at least 65% in 15 minutes and at least 90% in 45 minutes when tested in aqueous hydrochloric acid 0.1 N in a USP apparatus II at 50 rpm, 37° C. The dissolution profile of the capsules is similar to the profile of Imnovid®/Pomalyst®.

Example 4

Stability Results

TABLE 4

Stability results at 40° C./75% RH for Imnovid ®/Pomalyst ® capsules composition (4 mg/capsule) prepared according to Reference example 1 in different packaging materials

| | Packaging material | | | | | |
|---|---|---|---|---|---|---|
| | PVC/Al blister | | | HDPE bottle/PP cap | Al/Al blister | |
| | Time (months) | | | | | |
| | 0 | 3 | 6 | 6 | 3 | 6 |
| | Water content - KF (%) | | | | | |
| | 5.2 | 7.0 | 7.3 | 6.7 | 5.0 | 5.7 |

| Dissolution (%)* | Avg. | RSD | Avg. | RSD | Avg. | RSD | Avg. | RSD | Avg. | RSD | Avg. | RSD |
|---|---|---|---|---|---|---|---|---|---|---|---|---|
| in 5 min | 11 | 39.8 | 12 | 63.1 | 1 | 141.4 | 8 | 29.2 | 9 | 29.8 | 10 | 17.6 |
| in 10 min | 51 | 23.7 | 44 | 18.0 | 8 | 42.0 | 37 | 10.0 | 49 | 17.0 | 47 | 1.3 |
| in 15 min | 73 | 12.3 | 67 | 12.2 | 19 | 27.3 | 59 | 12.2 | 73 | 5.1 | 70 | 0.6 |
| in 20 min | 82 | 8.8 | 77 | 7.0 | 30 | 16.1 | 71 | 11.4 | 85 | 3.7 | 81 | 0.5 |
| in 30 min | 90 | 6.4 | 86 | 4.9 | 42 | 7.0 | 81 | 7.6 | 91 | 1.0 | 90 | 0.6 |
| in 45 min | 95 | 5.0 | 90 | 4.5 | 55 | 8.4 | 88 | 5.0 | 96 | 0.9 | 95 | 0.9 |
| Final spin 250 rpm - 10 min | 98 | 3.7 | 96 | 2.8 | 86 | 3.3 | 93 | 3.2 | 99 | 1.1 | 98 | 0.3 |

*0.1N HCl USP II 50 rpm, 37° C.

TABLE 5

Stability results at 40° C./75% RH for capsules (4 mg/capsule) prepared according to example 1 (comprising pomalidomide, microcrystalline cellulose and maltodextrin) in different packaging materials

| | Packaging material | | | | | |
|---|---|---|---|---|---|---|
| | PVC/Al blister | | | HDPE bottle/PP cap | Al/Al blister | |
| | Time (months) | | | | | |
| | 0 | 3 | 6 | 6 | 3 | 6 |
| | Water content - KF (%) | | | | | |
| | 6.3 | 8.2 | N.P. | 6.7 | 5.8 | 5.8 |

| Dissolution (%)* | Avg. | RSD | Avg. | RSD | Avg. | RSD | Avg. | RSD | Avg. | RSD | Avg. | RSD |
|---|---|---|---|---|---|---|---|---|---|---|---|---|
| in 5 min | 51 | 6.1 | 40 | 11.5 | 34 | 19.4 | 38 | 5.8 | 49 | 6.8 | 40 | 2.4 |
| in 10 min | 76 | 2.5 | 64 | 1.2 | 56 | 17.6 | 67 | 4.5 | 71 | 2.7 | 68 | 1.7 |
| in 15 min | 84 | 2.9 | 73 | 1.6 | 65 | 16.1 | 77 | 4.0 | 79 | 3.1 | 78 | 3.0 |
| in 20 min | 89 | 2.3 | 78 | 1.4 | 69 | 15.8 | 84 | 4.2 | 84 | 2.7 | 84 | 3.7 |
| in 30 min | 93 | 2.9 | 83 | 1.5 | 73 | 15.1 | 89 | 4.2 | 89 | 2.9 | 89 | 4.1 |
| in 45 min | 96 | 2.4 | 86 | 0.6 | 76 | 15.0 | 93 | 5.0 | 92 | 3.3 | 93 | 4.6 |
| Final spin 250 rpm - 10 min | 98 | 2.7 | 90 | 1.3 | 81 | 14.8 | 95 | 4.8 | 94 | 3.6 | 94 | 5.0 |

*0.1N HCl USP II 100 rpm, 37° C.

TABLE 6

Stability results at 40° C./75% RH for capsules (4 mg/capsule) prepared according to example 1 (comprising pomalidomide, microcrystalline cellulose and maltodextrin) in different packaging materials

| | Packaging material | | | | | | | | | |
|---|---|---|---|---|---|---|---|---|---|---|
| | Triplex 120/Al blister | | | | | HDPE bottle/PP cap | | | | |
| | Time (months) | | | | | | | | | |
| | 0 | | 3 | | 6 | | 3 | | 6 | |
| | Water content - KF (%) | | | | | | | | | |
| | 5.4 | | 7.2 | | 8.0 | | 6.2 | | 6.8 | |
| Dissolution (%)* | Avg. | RSD | Avg. | RSD | Avg. | RSD | Avg. | RSD | Avg. | RSD |
| in 5 min | 52 | 3.2 | 47 | 3.6 | 39 | 5.1 | 48 | 4.3 | 41 | 6.8 |
| in 10 min | 76 | 1.3 | 71 | 5.1 | 63 | 3.2 | 72 | 3.9 | 68 | 1.0 |
| in 15 min | 84 | 1.6 | 79 | 5.3 | 74 | 2.5 | 81 | 2.9 | 78 | 0.8 |
| in 20 min | 89 | 1.6 | 85 | 5.1 | 80 | 1.8 | 86 | 2.1 | 84 | 1.1 |
| in 30 min | 94 | 1.6 | 90 | 4.5 | 87 | 1.5 | 92 | 1.2 | 90 | 1.0 |
| in 45 min | 98 | 1.9 | 93 | 3.9 | 92 | 0.8 | 95 | 0.8 | 95 | 1.0 |
| Final spin 250 rpm - 10 min | 101 | 2.3 | 96 | 3.2 | 95 | 0.9 | 98 | 0.9 | 97 | 0.7 |

*0.1N HCl USP II 100 rpm, 37° C.

The invention claimed is:

1. A pharmaceutical composition comprising pomalidomide, maltodextrin and a filler, wherein the filler is microcrystalline cellulose and wherein the weight ratio of maltodextrin to filler ranges from 1:1 to 1:2, said composition is in the form of a capsule, and said composition exhibits a dissolution rate of at least 65% in 15 minutes and at least 90% in 45 minutes when tested in aqueous hydrochloric acid 0.1 N in a USP apparatus II at 50-100 rpm, 37° C.

2. The composition according to claim 1, wherein the maltodextrin has a dextrose equivalent (DE) of 11 to 14.

3. The composition according to claim 1, wherein pomalidomide is present in an amount of more than 2% by weight based on the total weight of the composition.

4. The composition according to claim 1, wherein the pomalidomide has a particle size distribution $D_{90}$ equal to or less than 15 μm.

5. The composition according to claim 1, further comprising a lubricant and optionally a disintegrant.

6. The composition according to claim 5, wherein the lubricant is sodium stearyl fumarate.

7. The composition according to claim 5, wherein the disintegrant is croscarmellose sodium.

8. The composition according to claim 1, wherein the capsule is a hard gelatin capsule.

9. The composition according to claim 2, further comprising a lubricant and optionally a disintegrant.

10. The composition according to claim 9, wherein the lubricant is sodium stearyl fumarate.

11. The composition according to claim 10, wherein said disintegrant is present and said disintegrant is croscarmellose sodium.

12. The composition according to claim 1, wherein said weight ratio of maltodextrin to filler is within the range of 1:1.2 to 1:1.5.

* * * * *